(12) United States Patent
Sharifi Sedeh et al.

(10) Patent No.: US 10,818,383 B2
(45) Date of Patent: Oct. 27, 2020

(54) HOSPITAL MATCHING OF DE-IDENTIFIED HEALTHCARE DATABASES WITHOUT OBVIOUS QUASI-IDENTIFIERS

(71) Applicant: KONINKLIJKE PHILIPS N.V., Eindhoven (NL)

(72) Inventors: Reza Sharifi Sedeh, Malden, MA (US); Yugang Jia, Winchester, MA (US); Daniel Robert Elgort, New York, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 360 days.

(21) Appl. No.: 15/771,726

(22) PCT Filed: Oct. 17, 2016

(86) PCT No.: PCT/IB2016/056201
§ 371 (c)(1),
(2) Date: Apr. 27, 2018

(87) PCT Pub. No.: WO2017/072623
PCT Pub. Date: May 4, 2017

(65) Prior Publication Data
US 2018/0358112 A1     Dec. 13, 2018

Related U.S. Application Data
(60) Provisional application No. 62/248,542, filed on Oct. 30, 2015.

(51) Int. Cl.
*G16H 10/60* (2018.01)
*G06F 16/11* (2019.01)
*G06F 19/00* (2018.01)

(52) U.S. Cl.
CPC .......... *G16H 10/60* (2018.01); *G06F 16/122* (2019.01); *G06F 19/00* (2013.01)

(58) Field of Classification Search
CPC ........ G16H 10/60; G06F 16/122; G06F 19/00
(Continued)

(56) References Cited

U.S. PATENT DOCUMENTS 10,096,075 B2 * 10/2018 Dvorak .................. G16H 50/70
2002/0073138 A1    6/2002 Beck
(Continued)

OTHER PUBLICATIONS

"Guidance Regarding Methods for De-identification of Protected Health Information in Accordance with the Health Insurance Portability and Accountability Act (HIPPA) Privacy Rule Table of Contents", Guidance on De-identification of Protected Health Information, Nov. 2012, whole document.

*Primary Examiner* — Dung K Chau (57) ABSTRACT

A database merger method (20) merges two or more anonymized healthcare databases (X, Y). Each anonymized healthcare database has personally identifying information anonymized including having medical care units replaced by medical care unit placeholders. In the database merger method, statistical patient feature distributions are computed for medical care unit placeholders in the anonymized healthcare databases. Medical care unit placeholders in different anonymized healthcare databases are matched by matching corresponding statistical patient feature distributions for the respective medical care unit placeholders. Patients in different anonymized healthcare databases are matched. The patient matching is performed within matched pairs of medical care unit placeholders to improve computational efficiency. A databases alignment table (16) is generated identifying the matched patients, or a merged anonymized healthcare database is generated that merges patient features (Continued)

in the different anonymized healthcare databases for each matched patient into a single patient entry.

20 Claims, 4 Drawing Sheets

(58) Field of Classification Search
USPC .......................................................... 707/769
See application file for complete search history.

(56) References Cited

U.S. PATENT DOCUMENTS

| | | |
|---|---|---|
| 2008/0195600 A1 | 8/2008 | Deakter |
| 2009/0177637 A1 | 7/2009 | Hollebeek |
| 2010/0161551 A1 | 6/2010 | Whynot |
| 2013/0304506 A1* | 11/2013 | Gallivan ................ G16H 50/30 705/3 |
| 2014/0379374 A1* | 12/2014 | Vinals ................... G16H 10/60 705/3 |
| 2015/0149208 A1* | 5/2015 | Lynch ................ G06F 21/6254 705/3 |
| 2015/0294089 A1* | 10/2015 | Nichols ................ G06F 3/0304 705/3 |
| 2018/0046679 A1 | 2/2018 | Sharifi Sedeh et al. |

* cited by examiner

| Feature | Database X accuracy | Database Y accuracy | Feature selected ? |
|---|---|---|---|
| Gender | 80% | 97% | No |
| Race | 99% | 97% | Yes |
| Mortality | 97% | 98% | Yes |
| Length of stay | 95% | 94% | Yes |
| Age | 97% | 99% | Yes |
| Primary diagnosis | 97% | 71% | No |
| Body weight | 99% | 98% | Yes |

HOSPITAL MATCHING OF DE-IDENTIFIED HEALTHCARE DATABASES WITHOUT OBVIOUS QUASI-IDENTIFIERS

CROSS-REFERENCE TO PRIOR APPLICATIONS

This application is the U.S. National Phase application under 35 U.S.C. § 371 of International Application No. PCT/IB2016/056201, filed on 17 Oct. 2016, which claims the benefit of U.S. Provisional Patent Application No. 62/248,542, filed on 30 Oct. 2015. These applications are hereby incorporated by reference herein.

FIELD

The following relates generally to the medical research and development arts, the medical database arts, medical data mining arts, and related arts.

BACKGROUND

Numerous areas of medical research and development leverage healthcare databases containing data on medical patients. Medical histories or other clinical data, patient billing data, administrative records pertaining to matters such as hospital bed occupancy, and so forth are maintained by hospitals or other medical facilities and/or by individual units such as the cardiac care unit (CCU), intensive care unit (ICU), or emergency admittance department. These databases store sensitive patient data that generally must be maintained confidentially under financial and/or medical privacy laws such as (in the United States) the Health Insurance Portability and Accountability Act (HIPAA).

It has also been recognized, however, that such databases are a rich source of information for performing a wide range of medical data analytics for clinical, hospital administrative, or other purposes. To enable a patient database to be used for such purposes while maintaining patient privacy, it is known to anonymize the database by removing patient-identifying information (PII). Information that needs to be anonymized includes patient name and/or medical identification number (suitably replaced by a randomly assigned number or the like), address, or so forth. However, other information that could, in combination, be PII should also be anonymized. For instance, it has been estimated that a combination of gender, date of birth and five-digit zip code can uniquely identify 87% of the population of the United States. Since gender and date of birth are likely to be useful for many medical analyses, this observation suggests that the zip code should be deemed PII that should be anonymized.

Information on the hospital also may be PII in combination with other information, and should be anonymized by replacement by a random identifier. Medical care unit information (e.g. hospital, care unit) is usually not removed entirely, but rather replaced by a random identifier for each hospital (or clinical ward, or other medical care unit) because many medical analytics seek correlations with medical care unit. For example, the success rate for heart transplants may strongly correlate with hospital or cardiac ward.

Even with the foregoing anonymization, certain "rare" patients may still be identifiable in the anonymized data. For example, consider a male patient who has died at the age of 115 in a hospital in the United States in year 2011. Although the combination of (gender, age, death date) may ordinarily not be sufficient to uniquely identify a patient, the extreme age of this particular patient at his death could make unique identification feasible, as there could be as few as a single male patient dying at age 115 in the United States in a given year. Similarly, a primary diagnosis of a very rare disease could be uniquely identifying in combination with a very few additional demographic data. Accordingly, the anonymization may further remove rare patient attributes that could be PII in combination with common demographic information. For example, such "rare" PII removal could include removal of age for patients older than some maximum age (e.g. older than 90 years old), removal of any primary diagnosis that is not on a chosen list of (sufficiently) common diagnoses, or so forth.

The anonymized database still provides a large body of information on which to perform a diverse range of medical analytics, while ensuring patient privacy.

SUMMARY

In one disclosed aspect, a device is disclosed for processing two or more anonymized healthcare databases in which each anonymized healthcare database has personally identifying information anonymized including having medical care units replaced by medical care unit placeholders. The device comprises an electronic processor programmed to perform a database merger process including the following operations. For each medical care unit placeholder in the anonymized healthcare databases, statistical feature distributions are computed for a set of patient features over the patients of the medical care unit placeholder. Medical care unit placeholders in one anonymized healthcare database (X) are matched with medical care unit placeholders in another anonymized healthcare database (Y) by matching the statistical feature distributions computed over the patients of the respective matched medical care unit placeholders. For each matched pair of medical care unit placeholders in the respective anonymized healthcare databases, patients of the medical care unit placeholder of one anonymized healthcare database (X) are matched with patients of the matched medical care unit placeholder of the other anonymized healthcare database (Y) by matching patient features of the respective matched patients.

In another disclosed aspect, a non-transitory storage medium stores instructions executable by an electronic data processing device to perform a database merger process that merges two or more anonymized healthcare databases. Each anonymized healthcare database has personally identifying information anonymized including having medical care units replaced by medical care unit placeholders. The database merger process comprises: computing statistical patient feature distributions over defined time intervals for medical care unit placeholders in the anonymized healthcare databases; matching medical care unit placeholders in the anonymized healthcare database X and the anonymized healthcare database Y by matching statistical patient feature distributions for the respective medical care unit placeholders; matching patients in the anonymized healthcare database X and the anonymized healthcare database Y in matched pairs of medical care unit placeholders; and generating one of (i) a databases alignment table identifying the matched patients and (ii) a merged anonymized healthcare database that merges patient features in the anonymized healthcare databases X, Y for each matched patient into a single patient entry.

In another disclosed aspect, a database merger method is disclosed that merges two or more anonymized healthcare databases. Each anonymized healthcare database has personally identifying information anonymized including having medical care units replaced by medical care unit placeholders. The database merger method comprises: computing statistical patient feature distributions for medical care unit placeholders in the anonymized healthcare databases; matching medical care unit placeholders in different anonymized healthcare databases by matching corresponding statistical patient feature distributions for the respective medical care unit placeholders; matching patients in different anonymized healthcare databases wherein the matching of patients is performed within matched pairs of medical care unit placeholders; and generating a databases alignment table identifying the matched patients or a merged anonymized healthcare database that merges patient features in the different anonymized healthcare databases for each matched patient into a single patient entry. The database merger method is suitably performed by a computer.

One advantage resides in providing larger databases for performing medical analytics by merging or combining two or more anonymized healthcare databases.

Another advantage resides in providing databases with more diverse information (e.g. combining clinical and financial data, for instance) for performing medical analytics by merging or combining two or more anonymized healthcare databases.

Another advantage resides in providing the foregoing advantages without compromising patient privacy.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION

As already described, an anonymized healthcare database can provide a large collection of information on which to perform a diverse range of medical analytics, while ensuring patient privacy. To appreciate the value of an anonymized healthcare database, it is noted that such a database may, in some instances, include data for in excess of a million patients or more. Such a database is a rich source for mining diverse correlations, statistical patterns, trends, and so forth.

However, a disadvantage recognized herein is that the data contained in an anonymized healthcare database is typically limited to data that are accessible by a single organization or group. For example, an electronic medical record (EMR) containing clinical data for all patients seen by a network of hospitals may be anonymized to provide a large healthcare database containing clinical data. Similarly, the same hospital network may have an administrative department that can generate an anonymized hospital administrative database containing information on bed occupancy rates, nurse workloads, and so forth. However, in some instances it may not be possible to generate a combined anonymized healthcare database that merges the EMR and hospital administrative databases of the hospital network. Such merging could only be performed by accessing both databases in order to perform synchronized anonymization—but HIPAA or other privacy laws may not permit such broad access. Interdepartmental cooperation is also likely to be needed to create such a combined anonymized clinical/administrative database, but this cooperation may not exist. As a consequence, medical researchers may have access only to separate anonymized EMR and administrative databases. If a research project requires integration of clinical and hospital administration data, these separate anonymized databases may be insufficient.

Similar problems can arise in other contexts. For example, two different hospital networks may independently create anonymized clinical databases from their respective EMR systems. However, they cannot create a combined anonymized EMR database because each hospital network is prohibited from access to the other hospital network's EMR. As a result, additional information that might be extracted from analysis of patients who have received medical care from both hospital networks is lost due to the independent anonymization processes.

Disclosed herein are approaches for overcoming these difficulties. In particular, approaches disclosed herein merge two or more anonymized healthcare databases after they have been anonymized. In other words, the anonymized database merging system disclosed herein has access only to the anonymized databases, and does not need access to the underlying non-anonymized patient data. Thus, the techniques disclosed herein can be applied to combine any two or more anonymized databases without consideration as to whether the owner of the database merging system has access to the underlying non-anonymized data. Further, the disclosed approaches do not rely upon de-anonymization or re-identification of anonymized data. They do not, for example, cross-reference against non-anonymized data sources to re-identify the anonymized data. Therefore, patient privacy is maintained in the merger of anonymized healthcare databases.

Figure 1:
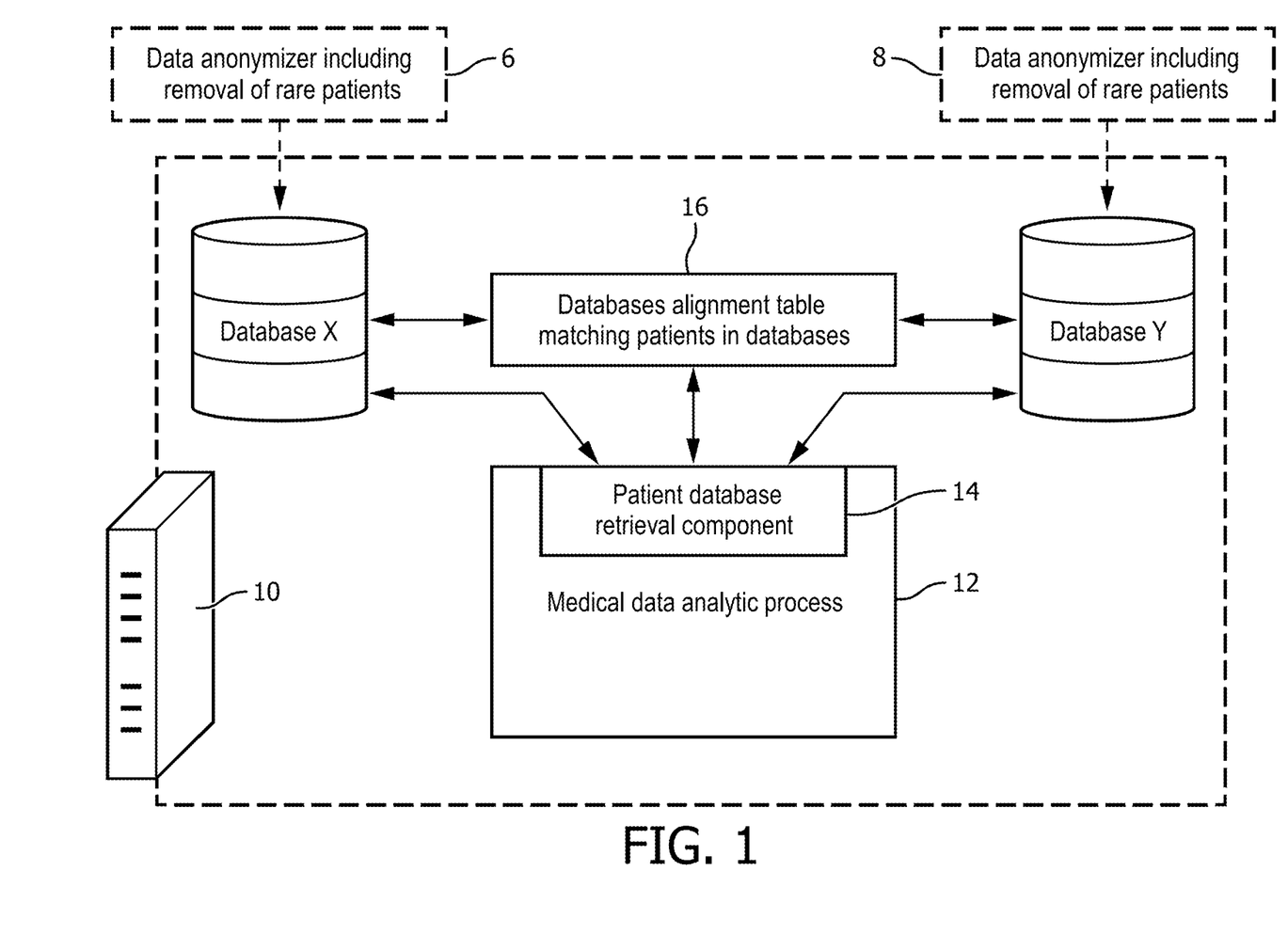
FIG. 1 diagrammatically illustrates a medical analytics system that leverages patient data merged from two anonymized healthcare databases.

With reference to FIG. 1, two anonymized healthcare databases are denoted "Database X" and "Database Y", respectively. The anonymized healthcare database X is generated by a data anonymizer 6, while the anonymized healthcare database Y is generated by a data anonymizer 8. The anonymizers 6, 8 are preferably automated (e.g. computer-implemented, with the computers programmed to remove certain classes or types of data) in order to anonymize large databases, e.g. a million patient entries or more in some embodiments. Optionally, one or both anonymizers 6, 8 may also include some manual processing, for example to remove certain rare patients or to address other unusual situations. The two anonymizers 6, 8 may or may not be identical, and may or may not anonymize the same information. In some embodiments, each anonymizer 6, 8 anonymizes personally identifying information (PII) that can immediately identify a patient, such as patient names, patient addresses, or so forth, as well as information that could potentially be PII in combination with other information, such as hospital name, zip code, or so forth. Where information may be PII in combination with other information, only a portion of the combination may need to be anonymized. For example, the combination of zip code, gender, and date of birth may be personally identifying—but by anonymizing only the zip code information acceptable patient anonymity may be achieved. The anonymizers 6, 8 may also remove rare information that could be identifying for certain patients. Such rare information may include, for example: any age over a certain maximum, e.g. 90 years old; diagnoses that are not among a list of common diagnoses; or so forth.

In general, the anonymization of a particular datum can be done by removing the data (redaction) or by replacing the data with a placeholder, the latter being preferable in situations where correlations with that particular type of information is desirably retained, albeit with anonymization. For example, in the disclosed techniques it is assumed that medical care unit (e.g. hospital or care unit) entries are replaced by placeholders that are internally consistent for the database. These placeholders are internally consistent within a given database, but vary essentially randomly between databases. For example, in Database X the hospital "Blackacre General Hospital" may be always replaced by the placeholder, e.g. "8243", while "Whiteacre Community Medical Center" may be always replaced by the placeholder "1238". In this example, every instance of medical care unit "Blackacre General Hospital" in Database X is replaced by (same) placeholder medical care unit "8243" and every instance of medical care unit "Whiteacre Community Medical Center" in Database X is replaced by the (same) placeholder medical care unit "1238". On the other hand, to continue the example for Database Y, each instance of medical care unit "Blackacre General Hospital" in Database Y may be replaced by the same placeholder medical care unit "EADF" (which is different from the placeholder "8243" used for Blackacre in anonymized Database X), and each instance of "Whiteacre Community Medical Center" may be replaced by the same placeholder medical care unit "JSDF" (which again is different from the placeholder "1238" used for Whiteacre in anonymized Database X). Such anonymization of medical care units by medical care unit placeholders that are internally consistent within the anonymized database enables a medical analytic operating on a database to identify correlations with a particular medical care unit while maintaining anonymity. For example, if Blackacre has a statistically significantly higher success rate for heart transplants than the average hospital, this will show up in Database X (assuming it stores heart transplant outcome data) as a statistically significantly higher success rate for heart transplants performed at anonymized hospital "8243".

On the other hand, some information may be anonymized by redaction, that is, removal. For example, residential address information may be redacted entirely, as this is highly identifying and useful correlations with residential address may not be expected. In a variant embodiment, if residential address correlations are expected to be a useful input for the medical data analytics, address anonymization may be performed by replacing each residential address by a broader geographical area, e.g. the residential city if this city has a sufficiently large population. A residential city or county with sufficiently small population may be redacted entirely to avoid retaining "rare" data that could be personally identifying, or may be replaced by a suitably larger geographical unit such as the residential state.

The anonymized Database X and the anonymized Database Y are each formatted in some structured format, for example in a relational database format or other structured database format, as spreadsheets, searchable column-delimited rich text files, or so forth. The anonymized Database X and the anonymized Database Y, or their merged combination as disclosed herein, is accessed by a medical data analytics system implemented on a computer 10, which may for example be a network-based server computer, a cloud computing resource, a server cluster, or so forth. The medical data analytics computer 10 executes at least one medical data analytic process 12 which mines the content of one or both anonymized Databases X, Y to identify correlations, statistical patterns, trends, or so forth in the data that may be of interest for improving clinical outcomes, hospital administrative efficiency, financial efficiency, or so forth; or that may be of interest for detecting poor clinical outcomes, administrative and/or financial inefficiency, or so forth. The medical data analytic process may be implemented as a dedicated computer program or may be constructed in a higher-level coded format such as a Structured Query Language (SQL) query or SQL program in embodiments in which the anonymized Databases X, Y are Relational Database Management System (RDBMS) relational databases. In addition to retrieving data from one or both anonymized Databases X, Y, the medical data analytic process 12 may perform a wide range of statistical, graphical, or other data processing operations such as computing a statistical mean, average, standard deviation or variance, or other statistical characteristic of data, plotting data using various formats (bar graph, pie graph, trend line, et cetera), or so forth.

With continuing reference to FIG. 1, the medical data analytic process 12 includes or accesses (e.g. via a function call, subroutine call, pointer link, or the like) a patient database retrieval component 14 that retrieves data from one or both anonymized Databases X, Y that meet some query criterion (e.g. defined by a SQL query). If the medical data analytic process 12 accesses only anonymized Database X, or only anonymized Database Y, then the patient database retrieval component 14 can directly access the appropriate database.

On the other hand, to access the merged anonymized Databases X, Y, the patient database retrieval component 14 references a database alignment table 16 that matches anonymized patients in the two Databases X, Y, and combines data from matched patients in the two Databases X, Y. If the matched patient entries in respective Databases X, Y both store the same value for a patient feature, then the retrieved value for this patient feature is this common value. If only one of the matched patient entries in respective Databases X, Y store a value for a patient feature, then the retrieved value for this patient feature is the one stored value. If the matched patient entries in respective Databases X, Y both store different values for a patient feature, this inconsistency can be resolved in various ways, such as by returning the average of the two values or by returning an error value for the patient feature. In one approach, the average value is returned if the two different stored values are sufficiently close (e.g. within a designated percentage), while an error value is returned if the two values differ more than this threshold percentage.

The merger of the Databases X, Y can be useful if, for example, Database X and Database Y store different information for a given anonymized patient. As illustration, if anonymized Database X is a clinical database and anonymized Database Y is a hospital administrative database, then the combination of a medical procedure performed on a patient (from Database X) and features of the surgical suite in which the surgery was performed (from Database Y) may be obtained for a single anonymized patient, thus enabling analytics such as impact of surgical facility on outcomes of the medical procedure. Advantageously, the database alignment table 16 is itself anonymized in that it does not identify any patient or rely upon PII in aligning patients of the two anonymized medical Databases X, Y. Moreover, construction of the database alignment table 16 does not rely upon de-anonymization or re-identification procedures.

In general, the medical data analytics computer 10 does not have access to the source database(s) from which the anonymized Databases X, Y are generated by the anonymizers 6, 8. This is diagrammatically indicated in FIG. 1 by placing the data anonymizers 6, 8 outside of the medical data analytics computer 10 and showing the data anonymizers 6, 8 using dotted lines. More generally, the Databases X, Y are anonymized and the medical data analytic process 12 does not have access to the underlying non-anonymized data. (For example, it is contemplated for the source non-anonymized databases to be accessible by the computer 10 but secured from access by the medical data analytic process 12 by suitable electronic data security procedures, e.g. data access levels, password protection, encryption, or so forth).

Figure 2:
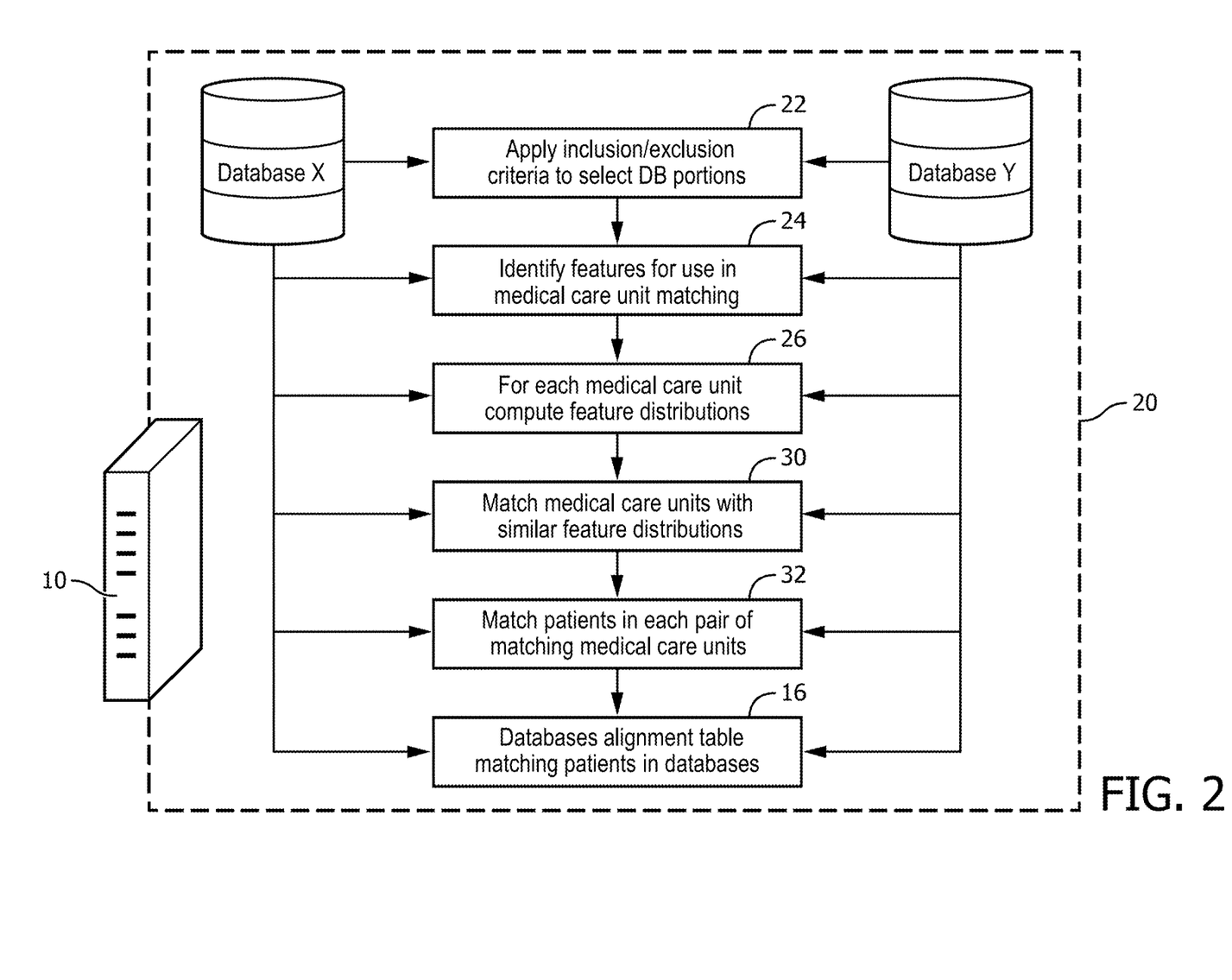
FIG. 2 diagrammatically illustrates a system for generating the databases alignment table of the medical analytics system of FIG. 1.

With reference to FIG. 2, a system for generating the database alignment table 16 is described. The system of FIG. 2 comprises a computer 10 that performs a merger process 20 that merges the two anonymized Databases X, Y by generating the database alignment table 16. In illustrative FIG. 2, the merger process 20 is implemented on the same computer 10 which also performs the medical data analytic process 12; however, this is not required and it is contemplated to instead perform the merger process 20 on a different computer than that which performs the medical data analytic process 12. As with the medical data analytic process 12, the merger process 20 also does not have access to the underlying non-anonymized data. For example, it is contemplated for the source non-anonymized databases to be accessible by the computer 10 but secured from access by the merger process 20 by suitable electronic data security procedures, e.g. data access levels, password protection, encryption, or so forth. Alternatively, the source non-anonymized databases may not be accessible at all by the computer 10. The merger process 20 performs the merger of anonymized Databases X, Y, that is, generates the database alignment table 16, using only information contained in the anonymized Databases X, Y. It may also be noted that while in the illustrative embodiment the output of the merger process 20 is the database alignment table 16, in other embodiments the output may be an actual merged database that contains a single patient entry for each matched pair of patients in the two Databases X, Y containing all (merged) information from both Databases X, Y from the matched pair of patients. (That is, the generated merged anonymized healthcare database merges patient features in the anonymized healthcare databases X, Y for each matched patient into a single patient entry).

In principle, the two Databases X, Y can be merged by exhaustive searching. In this exhaustive approach, starting with the first entry of Database X, every entry of Database Y is searched and the entry of Database Y that most closely aligns with the first entry of Database X is matched with the first entry of Database X (optionally only if the alignment meets some minimum threshold). This is repeated for the second entry of Database X, and so forth until all entries of Database X have been processed. However, this exhaustive approach is computationally intensive. For example, if Database X and Database Y each contain one million entries, then performing exhaustive searching entails $(1\times10^6)^2=10^{12}=1,000,000,000,000$ entry comparisons.

In merger approaches disclosed herein, this computational difficulty is overcome by the following approach. It is recognized herein that in most anonymized medical databases, medical care units (e.g. hospitals or wards) are anonymized by replacing each medical care unit with an internally consistent placeholder (e.g., every instance of a given hospital in a particular anonymized database is replaced by the same placeholder). Placeholders advantageously retain the ability to identify correlations, statistical trends, or the like at the hospital or ward level. Such correlations, trends or so forth cannot be extracted if the hospital name is redacted. Furthermore, use of internally consistent medical care unit placeholders in anonymizing medical care units can facilitate auditing if a controlling entity (which is not the medical data analytic process 12 and is not the merger process 20) collects and retains the information on which actual medical care unit corresponds to each medical care unit placeholder. Thus, if the medical data analytic process 12 were to (by way of illustration) identify some problem at a given hospital that impacts patient safety, the controlling entity could be consulted to identify the hospital and resolve the safety-related problem.

In merger approaches disclosed herein, the medical care units anonymized by internally consistent medical care unit placeholders are leveraged to match corresponding medical care units in different anonymized medical Databases X, Y. This matching is orders of magnitude lower in complexity than exhaustive per-patient matching. For example, the illustrative example of one million patients in each Database X, Y may correspond to (by way of illustration) 2,000 hospitals (or, more precisely, 2,000 hospital placeholders) for each Database X, Y if each hospital contributes an average of 500 patient entries. The hospital matching then entails $(2000)^2$ or four million comparisons (as compared with one trillion comparisons for exhaustive per-patient searching, which equates to a complexity reduction on the order of five orders of magnitude). With the hospitals matched, patient matching is performed for each pair of matched hospitals in Databases X, Y. In the immediate example, each hospital has 500 patient entries on average in each database, so this entails only about $(500)^2=250,000$ comparisons per hospital. The merger of the Databases X, Y is thus tractable even for large databases.

With continuing reference to FIG. 2, the illustrative merger process 20 includes the following operations. In an operation 22, inclusion/exclusion criteria are applied to select corresponding database portions of the Databases X, Y to be merged. The operation 22 may also include data format standardization, unit conversion, or other pre-processing. In an operation 24, a set of patient features for use in medical care unit matching are identified. In an operation 26, for each medical care unit a statistical distribution (e.g. probability distribution function) is computed for each patient feature over the patients of that medical care unit. The feature distributions may optionally be computed on a per-year basis (or on the basis of some other defined time interval, e.g. on a biennium basis, monthly basis, or so forth) to facilitate fair comparison where the Databases X, Y may span different time ranges. In such an approach, comparisons of the feature distribution profiles for different medical care units are made over time intervals for which both Databases X, Y have patient data. The feature distributions may optionally be modeled, for example by fitting to Gaussian model, spline curve fit, or other parameterized model, to reduce the number of values representing each distribution (e.g., a Gaussian model is parameterized by amplitude, mean, and variance values) and/or to facilitate analytical distribution comparisons and/or to allow processing the patient feature distributions as smooth continuous functions. The operation 26 generates a set of (per annum) feature distribution profiles (optionally represented by models) representing the various medical care units (or more precisely, the medical care unit placeholders), and these patient feature distribution profiles are then used in an operation 30 to match medical care units in respective Databases X, Y with similar patient feature distribution profiles. The operation 30 is premised on the expectation that the patient feature distributions of the patient population served by a medical care unit (on a per annum or other time interval basis) should be similar for the two Databases X, Y, since both Databases X, Y record data for many of the same patients. The operation 30 is further rationalized by the expectation that even if some patients recorded in Database X for a given medical care unit are not recorded in Database Y for that medical care unit (or vice versa), the underlying patient demographics served by the medical care unit are the same so that the feature distributions should be similar. With medical care units (or, more precisely, medical care unit placeholders) of respective Databases X, Y matched, in an operation 32 patients (or patient entries) in each matched pair of medical care units of respective Databases X, Y are matched. The patient matching operation 32 can be performed exhaustively since, as already explained, the patient matching matching operation 32 is performed over small sub-sets of the patients in Databases X, Y.

In the following, each of these operations 22, 24, 26, 30, 32 is described in additional detail and/or by way of illustrative example(s) in the following.

The operation 22 applies inclusion and exclusion criteria. In order to match hospitals (or other medical care units) from two different big de-identified healthcare Databases X, Y, the subsets of the two databases that are possibly related are extracted in the operation 22. For example, if one database covers only the data of Medical-surgical and Burn-Trauma intensive care unit (ICU) patients, from the other database, the subset of patients who were admitted to Medical-surgical and Burn-Trauma ICU wards during their hospitalizations are suitably considered. The operation 22 may optionally include other pre-processing such as standardization of date representations.

The feature selection operation 24 identifies a subset of non-uniquely identifying features (since the Databases X, Y are anonymized) for which reasonably accurate probability density functions or other statistical distributions can be generated. The identified set of patient features is used in the subsequent medical care unit matching. To be included in the set of patient features, the feature must be present in both Databases X, Y. Some potentially suitable features are tabulated in FIG. 3. Furthermore, the inventors have found that some anonymized healthcare databases contain high rates or fractions of inaccurate information for certain patient features, apparently due to data entry and/or transcription errors, and patient features with substantial inaccuracy are preferably omitted from the set of patient features used to statistically characterize medical care units. Although the anonymization makes accuracy assessment difficult, various approaches can be used to assess (statistically) the accuracy of a given feature in a given anonymized database. For example, if a patient is indicated as having gender "male" and primary diagnosis "pregnancy", one or both of these data are incorrect. Incredible feature values may also be recognized as erroneous, e.g. patient age of 200 years old. Incredible feature distributions may also be recognized as erroneous—for example, if a (placeholder) hospital has patient length of stay of 30 days for every patient, this is almost certainly data error. For the purpose of feature selection, an omitted value for a feature may optionally be considered to be an "error" since missing feature data reduces usefulness of the patient feature for characterizing medical care units. For example, if age is only recorded for two-thirds of the patients this is a high error rate and makes age less useful for characterizing medical care units.

Figure 3:
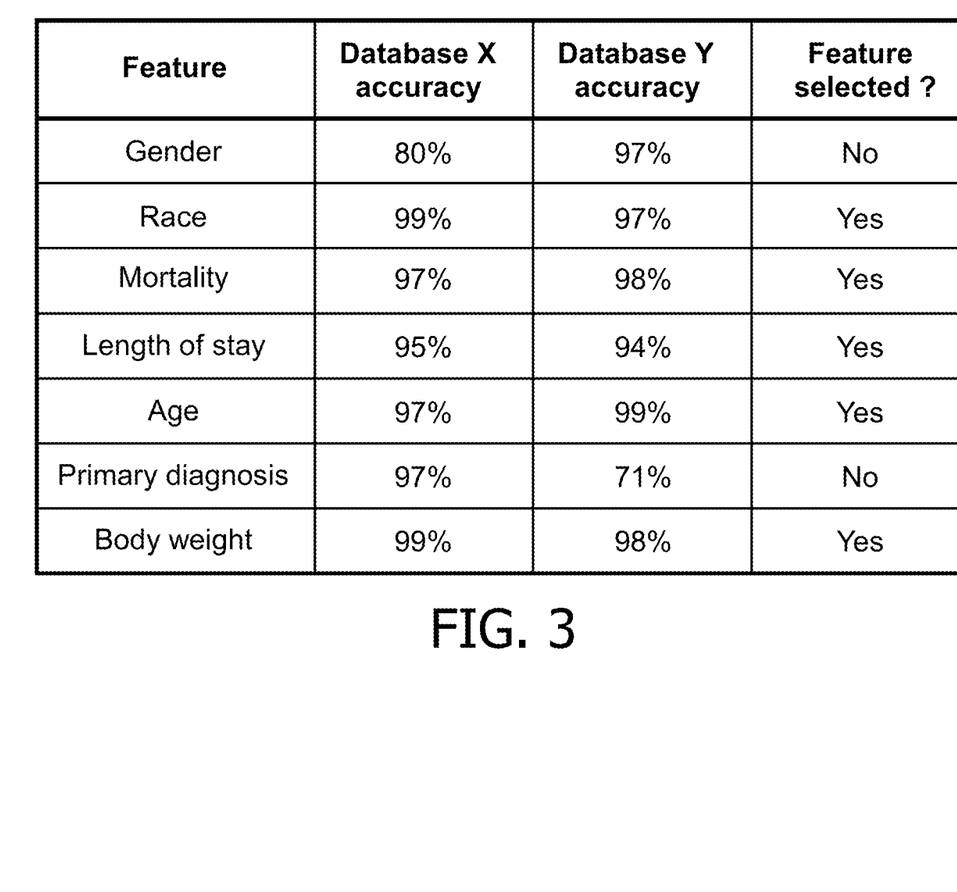
FIG. 3 shows a prophetic feature selection table.

With brief reference to FIG. 3, for example, a prophetic example of accuracy of the Databases X, Y for various potential features is tabulated. As seen in FIG. 3, Database X exhibits low accuracy of 80% for gender (i.e., 20% of gender entries are determined to be wrong), while Database Y has low accuracy of 71% for primary diagnosis (i.e. 29% of primary diagnoses are determined to be wrong). All other feature accuracies tabulated in FIG. 3 above 90%. Thus, the features are identified from the tabulation of FIG. 3 as "race", "mortality", length of stay", "age", and "body weight", but not "gender" and not "primary diagnosis". More generally, for a feature to be selected in the operation 24, the accuracy of the feature in both Databases X, Y should be high.

Figure 4:
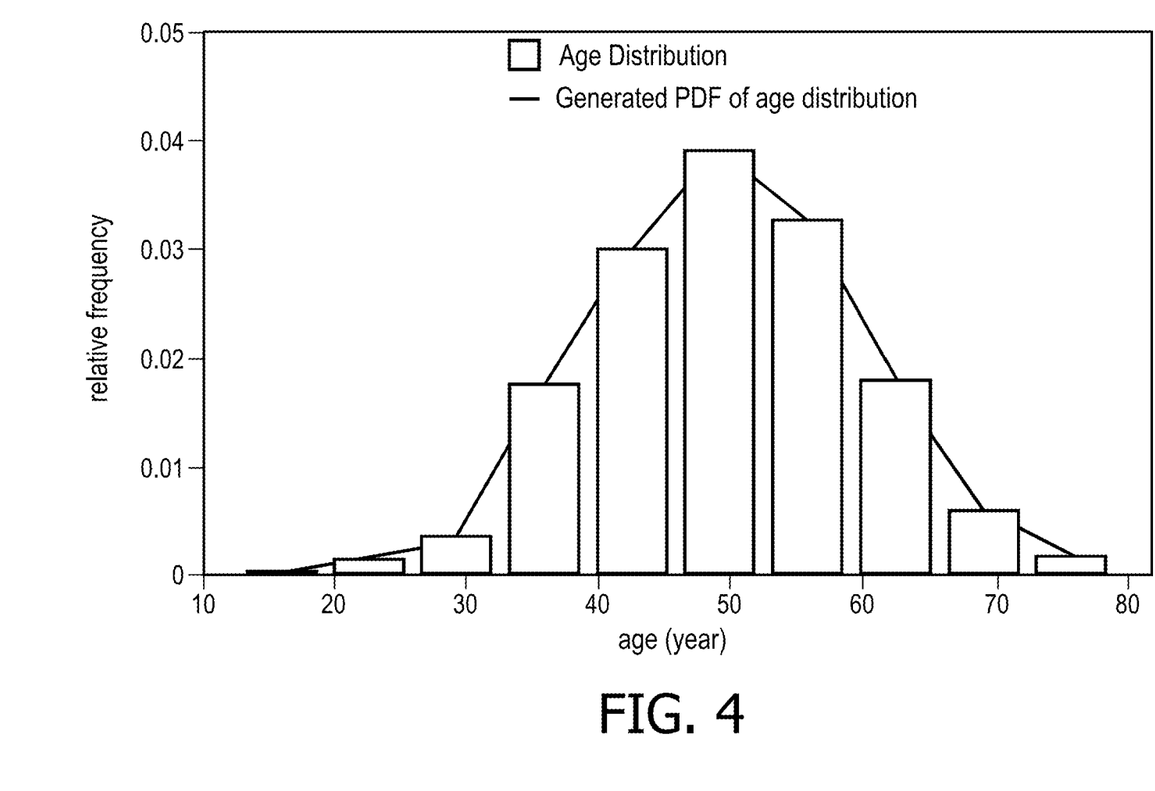
FIG. 4 shows a prophetic age distribution for a medical care unit.

The operation 26 computes statistical distributions for the features identified in the operation 24. FIG. 4 illustrates a prophetic probability distribution function (PDF) for age. In this illustrative example, patient age is grouped into nine age bins spanning the age range 20-80 years so as to form a histogram, which is seen to resemble a bell-shaped curve. Optionally, the histogram may be fitted to a parameterized model as shown by the line in FIG. 4, such as a Gaussian model, spline curve fit or the like, to reduce the number of parameters and/or facilitate analytical computation and/or to allow processing of the statistical feature distributions as smooth, continuous functions.

The medical care unit matching operation 30 matches medical care unit placeholders in one anonymized healthcare Database X with medical care unit placeholders in another anonymized healthcare Database Y by matching statistical feature distributions computed over the patients of the respective matched medical care unit placeholders. In one illustrative approach, the medical care unit matching operation 30 suitably applies a statistical test such as a Kolmogorov-Smirnov test, a Chi-Squared test, or so forth to compute similarity metrics for corresponding feature distributions of two (placeholder) medical care units in respective Databases X, Y. The Kolmogorov-Smirnov test or a Chi-Squared test generates a probability value (p-value) for the assumption that each two generated PDFs of each feature for a specific year for (e.g.) Hospital A from Database X and Hospital B from Database Y to be from the same distribution. A similarity metric between Hospital A and Hospital B for the specific year can be created by multiplying the p-values of the set of features for the same year (2010 is used in the following example). For example, if (as in illustrative FIG. 3) five features are selected in operation 24 ("race", "mortality", "length of stay", "age", and "body weight"), the similarity metric between Hospital A and Hospital B in year 2010 would be equal to $S_{2010,A\&B} = p_{2010,A\&B}^1 \times p_{2010,A\&B}^2 \times p_{2010,A\&B}^3 \times p_{2010,A\&B}^4 \times p_{2010,A\&B}^5$ where the superscript indexes patient feature and the subscript identifies the year (or other defined time interval over which the distribution profiles are computed). Then for each year, hospitals from the two Databases X, Y are linked based on the highest values of pair-wise similarity metrics. Two (placeholder) hospitals in respective Databases X, Y are matched with each other in operation 30 if their similarity metric $S_{year,A\&B}$ exceeds a chosen threshold over a threshold percent of the years compared (e.g. 75% of the compared years in one embodiment). This is merely one illustrative matching criterion, and other matching criteria computed as an aggregative metric of similarity of the feature distributions in the compared medical care units are contemplated.

The patient matching operation 32 then matches corresponding patients in each matched pair of medical care units in respective Databases X, Y identified by the medical care unit matching operation 30 by matching patient features of the respective matched patients. In an exhaustive approach, starting with the first patient of Hospital A in Database X, every patient of matched Hospital B in Database Y is searched and the patient of Hospital B in Database Y whose patient features most closely match with corresponding patient features of the first patient of Hospital A in Database X is matched with the first patient of Hospital A in Database X (optionally only if the alignment meets some minimum threshold). This is repeated for each succeeding patient of Hospital A in Database X until all patients of Hospital A in Database X have been processed. The patient matching 32 typically uses the same patient features that were identified in the operation 24 for use in matching medical care units, although this is not essential (e.g., additional, fewer, or different features may be used in the patient matching 32). In a variant approach, patients are first binned by a chosen feature such as age (possibly with some bin overlap), and the comparisons are performed for patients in corresponding bins. If the bins are chosen appropriately, this can reduce the overall number of comparisons.

The resulting patient matches are then used to construct the database alignment table 16, e.g. by storing a look-up table identifying patients in Database Y that match patients in Database X and vice versa. Alternatively, the merger can be performed by generating a new merged database that combines data from respective Databases X, Y in accordance with the results of the patient matching operation 32.

Because the medical care unit matching operation 30 leverages the feature distributions generated by the operation 26, this matching is not dependent upon availability of "rare" data that is sometimes redacted from the anonymized databases (e.g. age values over 90 years, rare primary diagnoses, et cetera). At most, redaction of these rare data, if they correspond to features, impacts statistical accuracy of those features. However, rare values by definition occur rarely, and so their redaction is unlikely to significantly impact the statistical accuracy of the feature in the database (e.g. as tabulated in FIG. 3).

As previously noted, the medical care units are most commonly recorded as hospitals, but may alternatively be other medical care units such as hospital networks, individual care wards, or so forth. It is also noted that the merger of Databases X, Y may not match every patient in Database X with a patient in Database Y, or vice versa. This could be because a patient has no match in the other database, or because the operation 32 was unable to find the match with sufficient probability. In the case of an unmatched patient, the database alignment table 16 suitably stores a special value (e.g. <null>) to indicate no match.

It will also be appreciated that the foregoing processing can be repeated to merge three (or more) healthcare databases. Various approaches can be used. For example, given three Databases X, Y, and Z, the processing can entail: (i) merging Databases X, Y; (ii) merging Databases X, Z; and (iii) merging Databases Y, Z. An optional consistency check can be performed, e.g. if patient A in Database X is matched with patient M in Database Y in operation (i) and patient A in Database X is matched with patient F in Database Z in operation (ii), then to be consistent the operation (iii) should match patient M in Database Y with patient F in Database Z.

It will be appreciated that the disclosed functionality of the medical data analytic process 12 and/or of the database merger process 20 as described herein may be embodied as a non-transitory storage medium storing instructions that are readable and executable by an electronic processor 10 to perform the disclosed functionality. The non-transitory storage medium may, for example, comprise a hard disk drive or other magnetic storage medium, an optical disk or other optical storage medium, a flash memory, read-only memory (ROM), or other electronic storage medium, various combinations thereof, or so forth.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A device for processing two or more anonymized healthcare databases in which each anonymized healthcare database has personally identifying information anonymized including having medical care units replaced by medical care unit placeholders, the device comprising:
　an electronic processor programmed to perform a database merger process including the operations of:
　for each medical care unit placeholder in the anonymized healthcare databases, computing statistical feature distributions for a set of patient features over the patients of the medical care unit placeholder;
　matching medical care unit placeholders in one anonymized healthcare database with medical care unit placeholders in another anonymized healthcare database by matching statistical feature distributions computed over the patients of the respective matched medical care unit placeholders; and
　for each matched pair of medical care unit placeholders in the respective anonymized healthcare databases, matching patients of the medical care unit placeholder of one anonymized healthcare database with patients of the matched medical care unit placeholder of the other anonymized healthcare database by matching patient features of the respective matched patients.

2. The device of claim 1 wherein the database merger process includes the further operation of:
　generating a databases alignment table identifying the matched patients.

3. The device of claim 2 wherein the electronic processor is further programmed to perform a data retrieval operation including:
　referencing the databases alignment table to identify matched patients; and
　returning a merger of the patient features stored for the matched patients in the respective databases.

4. The device of claim 1 wherein the database merger process includes the further operation of:
　generating a merged database that merges patient features in the anonymized healthcare databases for each matched patient into a single patient entry.

5. The device of claim 1 wherein the computing of statistical feature distributions for a set of patient features over the patients of the medical care unit placeholder includes fitting the statistical feature distributions to parameterized models.

6. The device of claim 1 wherein:
the computing of statistical feature distributions includes computing statistical feature distributions per annum; and
the matching of medical care unit placeholders includes matching medical care unit placeholders in one anonymized healthcare database with medical care unit placeholders in another anonymized healthcare database by matching corresponding per annum statistical feature distributions.

7. The device of claim 6 wherein the matching of medical care unit placeholders includes:
computing a probability value (p-value) for the assumption that each two corresponding per annum statistical feature distributions are from the same distribution; and
matching medical care unit placeholders in one anonymized healthcare database with medical care unit placeholders in another anonymized healthcare database if the p-values exceed a threshold for a threshold fraction of years.

8. The device of claim 7 wherein the p-value is computed using a Kolmogorov-Smirnov test or a Chi-Squared test.

9. The device of claim 1 wherein the database merger process further includes the operation of selecting the set of patient features as a sub-set of the set of patient features contained in every one of the two or more anonymized healthcare databases for which an estimated statistical accuracy of the patient feature in every one of the two or more anonymized healthcare databases exceeds a threshold.

10. The device of claim 1 wherein the database merger process operates on the two or more anonymized healthcare databases but does not operate on underlying non-anonymized patient data from which the two or more anonymized healthcare databases were generated by anonymization.

11. A non-transitory storage medium storing instructions executable by an electronic data processing device to perform a database merger process that merges two or more anonymized healthcare databases in which each anonymized healthcare database has personally identifying information anonymized including having medical care units replaced by medical care unit placeholders, the database merger process comprising:
computing statistical patient feature distributions over defined time intervals for medical care unit placeholders in the anonymized healthcare databases;
matching medical care unit placeholders in the anonymized healthcare database and the anonymized healthcare database by matching statistical patient feature distributions for the respective medical care unit placeholders;
matching patients in the anonymized healthcare database and the anonymized healthcare database in matched pairs of medical care unit placeholders; and
generating one of (i) a databases alignment table identifying the matched patients and (ii) a merged anonymized healthcare database that merges patient features in the anonymized healthcare databases for each matched patient into a single patient entry.

12. The non-transitory storage medium of claim 11 wherein the computing of statistical patient feature distributions includes generating statistical patient feature distribution histograms and fitting the histograms to parameterized models.

13. The non-transitory storage medium of claim 11 wherein:
the statistical patient feature distributions are computed for defined time intervals, and the matching of medical care unit placeholders is performed by matching statistical patient feature distributions for common time intervals for which both databases contain patient data for the respective medical care unit placeholders.

14. The non-transitory storage medium of claim 13 wherein the define time intervals are per annum time intervals.

15. The non-transitory storage medium of claim 13 wherein the matching of medical care unit placeholders includes:
computing a probability values (p-values) for the assumption that the statistical patient feature distributions computed for each common time interval are from the same distribution; and
matching medical care unit placeholders using a similarity metric computed by aggregating the p-values computed for the common time intervals.

16. The non-transitory storage medium of claim 15 wherein the p-value is computed using a Kolmogorov-Smirnov test or a Chi-Squared test.

17. The non-transitory storage medium of claim 11 wherein the database merger process further comprises:
estimating statistical accuracy of patient features that are common to the two or more anonymized healthcare databases; and
selecting a set of patient features for which the statistical patient feature distributions are computed by selecting patient features having high estimated statistical accuracy in every one of the two or more anonymized healthcare databases.

18. The non-transitory storage medium of claim 11 wherein the database merger process operates on the two or more anonymized healthcare databases but does not operate on underlying non-anonymized patient data from which the two or more anonymized healthcare databases were generated by anonymization.

19. A database merger method that merges two or more anonymized healthcare databases in which each anonymized healthcare database has personally identifying information anonymized including having medical care units replaced by medical care unit placeholders, the database merger method comprising:
computing statistical patient feature distributions for medical care unit placeholders in the anonymized healthcare databases;
matching medical care unit placeholders in different anonymized healthcare databases by matching corresponding statistical patient feature distributions for the respective medical care unit placeholders;
matching patients in different anonymized healthcare databases wherein the matching of patients is performed within matched pairs of medical care unit placeholders; and
generating a databases alignment table identifying the matched patients or a merged anonymized healthcare database that merges patient features in the different anonymized healthcare databases for each matched patient into a single patient entry;
wherein the database merger method is performed by a computer.

20. The database merger method of claim 19 further comprising:
estimating statistical accuracy of patient features that are common to the two or more anonymized healthcare databases; and
selecting a set of patient features for which the statistical patient feature distributions are computed by selecting patient features with high estimated statistical accuracy in every one of the two or more anonymized healthcare databases.

* * * * *